_United States Patent_ [19]

Meyer et al.

[11] 3,932,645
[45] Jan. 13, 1976

[54] PHARMACEUTICAL COMPOSITIONS CONTAINING UNSYMMETRICAL ESTERS OF 1,4-DIHYDROPYRIDINE 3,5-DICARBOXYLIC ACID

[75] Inventors: Horst Meyer; Friedrich Bossert, both of Wuppertal-Elberfeld; Wulf Vater, Opladen; Kurt Stoepel, Wuppertal-Vohwinkel, all of Germany

[73] Assignee: Farbenfabriken Bayer AG, Germany

[22] Filed: Sept. 20, 1973

[21] Appl. No.: 398,982

Related U.S. Application Data

[62] Division of Ser. No. 242,239, April 7, 1972, Pat. No. 3,799,934.

[30] Foreign Application Priority Data

Apr. 10, 1971 Germany............................ 2117571

[52] U.S. Cl. ................ 424/266; 424/226; 424/251; 424/258; 424/263

[51] Int. Cl.² ...................................... A61K 31/455
[58] Field of Search ............ 424/263, 266, 251, 258

[56] References Cited
UNITED STATES PATENTS
3,470,297    9/1969    Bossert et al. ...................... 424/263

Primary Examiner—V. D. Turner

[57] ABSTRACT

Pharmaceutical compositions containing unsymmetrical esters of 1,4-dihydropyridine 3,5-dicarboxylic acids as the active ingredient and methods of using same. The said ingredients are unsymmetrical 1,4-dihydropyridine 3,5-dicarboxylates which are substituted at position-4 of the dihydropyridine nucleus by phenyl which contains at least one nitro, cyano, azido, alkylthio, or alkylsulphonyl substituent. The compositions have a cardiovascular activity which makes them useful for effecting coronary vascular dilation and, also, they have utility in the treatment of hypertension.

28 Claims, No Drawings

PHARMACEUTICAL COMPOSITIONS CONTAINING UNSYMMETRICAL ESTERS OF 1,4-DIHYDROPYRIDINE 3,5-DICARBOXYLIC ACID

This is a division of application Ser. No. 242,239 filed Apr. 7, 1972, now U.S. Pat. No. 3,799,934 dated Mar. 26, 1974.

The present invention relates to unsymmetrical esters of 1,4-dihydropyridine-dicarboxylic acids, to processes for their production and to their use coronary and antihypertensive agents.

Although a variety of esters of 4-substituted-1,4-dihydropyridine-3,5-dicarboxylic acids are known [see for example Knoevenagel, Ber. 31, 743 (1898) and U.S. Pats. Nos. 3,325,505; 3,441,648; 3,485,847; 3,488,359 and 3,511847], all of these have been symmetrical with respect to the ester groups in the 3- and 5-positions. Indeed up to the present, the preparative methods available to the art for such esters were limited to the preparation of symmetrical esters.

The present invention is directed at compounds of the formula:

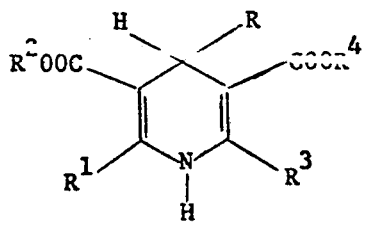

wherein
R is mono-, di- or trisubstituted phenyl in which the substituents are selected from the group consisting of nitro, cyano, azido, —S(O)$_n$-lower alkyl in which $n$ has a value of 0, 1 or 2, lower alkyl, lower alkoxy or halogeno, at least one of said substituents being nitro, cyano, azido or —S(O)$_n$-lower alkyl; or an unsubstituted or substituted ring system selected from the group consisting of naphthyl, quinolyl, isoquinolyl, pyridyl, pyrimidyl, thenyl, furyl, or pyrryl, in which when substituted the substituent is lower alkyl or lower alkoxy;

each of R$^1$ and R$^3$, independent of the other, is hydrogen or lower alkyl;

R$^2$ is lower alkyl, lower alkenyl, lower alkynyl, or lower alkoxy(lower alkyl);

R$^4$ is lower alkyl, lower alkenyl, lower alkynyl, or lower alkoxy(lower alkyl), R$^4$ being different from R$^2$, or a pharmaceutically acceptable acid addition salt thereof.

The term alkyl denotes a univalent saturated branched or straight hydrocarbon chain containing from 1 to 18 carbon atoms. Representative of such alkyl groups are thus methyl, ethyl, propyl, isopropyl, butyl, isobutyl, sec.butyl, tert.butyl, pentyl, isopentyl, neopentyl, tert.pentyl, hexyl, isohexyl, heptyl, octyl, nonyl, decyl, undecyl, dodecyl, tridecyl, tetradecyl, pentadecyl, hexadecyl, heptadecyl, octadecyl, and the like.

The term lower alkyl denotes a univalent saturated branched or straight hydrocarbon chain containing from 1 to 6 carbon atoms. Representative of such lower alkyl groups are thus methyl, ethyl, propyl, isopropyl, butyl, isobutyl, sec.butyl, tert.butyl, pentyl, isopentyl, neopentyl, tert.pentyl, hexyl, and the like.

The term lower alkenyl denotes a univalent branched or straight hydrocarbon chain containing from 2 to 6 carbon atoms and nonterminal ethylenic unsaturation as, for example, vinyl, allyl, isopropenyl, 2-butenyl, 3-methyl-2-butenyl, 2-pentenyl, 3-pentenyl, 2-hexenyl, 4-hexenyl, and the like.

The term lower alkynyl denotes a univalent branched or straight hydrocarbon chain containing from 2 to 6 carbon atoms and nonterminal acetylenic unsaturation as, for example, ethynyl, 2-propynyl, 4-pentynyl, and the like.

As indicated, the present invention also pertains to the physiologically acceptable non-toxic acid addition salts of these basic compounds. Such salts include those derived from organic and inorganic acids such as, without limitation, hydrochloric acid, hydrobromic acid, phosphoric acid, sulfuric acid, methane sulphonic acid, acetic acid, tartaric acid, lactic acid, succinic acid, citric acid, malic acid, maleic acid, sorbic acid, aconitic acid, salicylic acid, phthalic acid, embonic acid, enanthic acid, and the like.

The compounds of the present invention can exist as optical isomers and both the racemates of these isomers and the individual isomers themselves are within the scope of the present invention. The racemates can be separated into their individual isomers through the well known technique and forming diastereoisomeric salts with optically active acids.

As discussed in greater detail below, the compounds of the present invention are valuable cardiovascular agents possessing in particular coronary vascular dilation properties together with antihypertensive properties.

These compounds are prepared through treatment of an ylidene-β-ketocarboxylic acid of the formula:

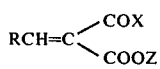

with either (a.) an enaminocarboxylic acid ester of the formula:

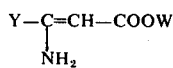

or (b.) a β-ketocarboxylic acid ester of the formula:
Y—COCH$_2$COOW
and ammonia. In the foregoing formulas, X corresponds to one of R$^1$ and R$^3$ and Y corresponds to the other of R$^1$ and R$^3$ while Z corresponds to one of R$^2$ and R$^4$ and W corresponds to the other of R$^2$ and R$^4$.

The foregoing processes can be diagrammatically depicted as follows:

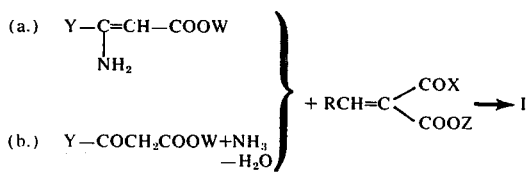

The process of the invention are generally carried out utilizing water or any inert organic solvent as diluent. Preferred organic solvents for this purpose include alcohols, such as methanol, ethanol and propanol, ethers such as dioxane, diethylether or tetrahydrofuran. Highly polar solvents such as glacial acetic acid, pyridine, dimethylformamide dimethylsulfoxide and acetonitrile can also be employed. The reaction temperatures can be varied over a substantial range but in general, the reaction is carried out at from about 20° to about 200°C. Conveniently the reaction is conducted at the boiling point of the solvent. Either normal pressure or elevated pressure can be employed, normal pressure being more convenient. With the exception of ammonia which is generally used in excess, the reactants are employed in approximately stoichiometric amounts.

The requisite starting materials are either known to the art or can be readily prepared through conventional synthetic methods. As representative starting materials can be mentioned a. Ylidene-β-ketocarboxylic acids
2'-nitrobenzylideneacetoacetic acid methyl ester,
2'-nitrobenzylideneacetoacetic acid methyl ester,
3'-nitrobenzylideneacetoacetic acid methyl ester,
3'-nitrobenzylideneacetoacetic acid ethyl ester,
3'-nitrobenzylideneacetoacetic acid isopropyl ester,
2'-cyanobenzylideneacetoacetic acid methyl ester,
2'-cyanobenzylideneacetoacetic acid ethyl ester,
2-cyanobenzylideneacetoacetic acid propyl ester,
2'-cyanobenzylideneacetoacetic acid allyl ester,
4'-nitrobenzylideneacetoacetic acid methyl ester,
3'-cyanobenzylideneacetoacetic acid ethyl ester,
3'-cyanobenzylideneacetoacetic acid propargyl ester,
4'-cyanobenzylideneacetoacetic acid ethyl ester,
3'-nitro-4'-chlorobenzylideneacetoacetic acid t-butyl ester,
3'-nitro-4'-chlorobenzylideneacetoacetic acid isopropyl ester,
3'-nitro-6'-chlorobenzylideneacetoacetic acid cyclohexyl ester,
3'-nitro-6'-chlorobenzylideneacetoacetic acid ethyl ester,
3-nitro-4'-methoxybenzylideneaceteacetic acid methyl ester,
2'-nitro-4'-methoxybenzylideneacetoacetic acid methyl ester,
2'-cyano-4'-methylbenzylideneacetoacetic acid ethyl ester,
2'-azidobenzylideneacetoacetic acid methyl ester,
2'-azidobenzylideneacetoacetic acid ethyl ester,
3'-azidobenzylideneacetoacetic acid propargyl ester,
4'-azidobenzylideneacetoacetic acid methyl ester,
4'-methylmercaptobenzylideneacetoacetic acid ethyl ester,
2'-methylmercaptobenzylideneacetoacetic acid ethyl ester,
2'-sulphinylmethylbenzylideneacetoacetic acid methyl ester,
2'-sulphonylmethylbenzylideneacetoacetic acid isopropyl ester,
4'-sulphonylmethylbenzylideneacetoacetic acid ethyl ester,
(1'-naphthylidene)-acetoacetic acid methyl ester,
(1'-naphthylidene)acetoacetic acid ethyl ester,
(2'-naphthylidene)acetoacetic acid ethyl ester,
2'-ethoxy-(1'-naphthylidene)acetoacetic acid methyl ester,
2'-methoxy-(1'-naphthylidine) acetoacetic acid ethyl ester,
5'-bromo-(1'-naphthylidene)acetoacetic acid methyl ester,
(2'-quinolyl)-methylideneacetoacetic acid ethyl ester,
(3'-quinolyl)methylideneacetoacetic acid methyl ester,
(4'-quinolyl)-methylideneacetoacetic acid ethyl ester,
(8'-quinolyl)methylideneacetoacetic acid ethyl ester,
(1'-isoquinolyl)methylideneacetoacetic acid methyl ester,
(3'-isoquinolyl)methylideneacetoacetic acid methyl ester,
α-pyridylmethylideneacetoacetic acid methyl ester,
α-pyridylmethylideneacetoacetic acid ethyl ester,
α-pyridylmethylideneacetoacetic acid allyl ester,
α-pyridylmethylideneacetoacetic acid propargyl ester,
α-pyridylmethylideneacetoacetic acid cyclohexyl ester,
α-pyridylmethylideneacetoacetic acid α-methoxyethyl ester,
α-pyridylmethylideneacetoacetic acid ethyl ester,
γ-pyridylmethylideneacetoacetic acid methyl ester,
6'-methyl-α-pyridylmethylideneacetoacetic acid ethyl ester,
4',6'-dimethoxy-(5'-pyrimidyl)-methylideneacetoacetic acid ethyl ester,
(2'-thenyl)-methylideneacetoacetic acid ethyl ester,
(2'-furyl)-methylideneacetoacetic acid allyl ester,
(2'-pyrryl)-methyliden-acetoacetic acid methyl ester,
3'-nitro-α-benzylidenepropionylacetic acid ethyl ester and
α-pyridylmethylidenepropionylacetic acid methyl ester.

b. β-Ketocarboxylic acid esters
Formylacetic acid ethyl ester,
acetoacetic acid methyl ester,
acetoacetic acid ethyl ester,
acetoacetic acid propyl ester,
acetoacetic acid isopropyl ester,
acetoacetic acid butyl ester,
acetoacetic acid t-butyl ester,
acetoacetic acid (α- or β-)-methoxyethyl ester,
acetoacetic acid (β- or β-)-ethoxyethyl ester,
acetoacetic acid (α- or β-)-propoxyethyl ester,
acetoacetic acid (α- or β-)-hydroxyethyl ester,
acetoacetic acid allyl ester,
acetoacetic acid propargyl ester,
acetoacetic acid cyclohexyl ester,
propionylacetic acid methyl ester,
propionylacetic acid ethyl ester,
propionylacetic acid isopropyl ester and
butyrylacetic acid ethyl ester.

c. Enaminocarboxylic acid esters
β-Aminocrotonic acid methyl ester,
β-Aminocrotonic acid ethyl ester,
β-aminocrotonic acid isopropyl ester,
β-aminocrotonic acid propyl ester,
β-aminocrotonic acid allyl ester,
β-aminocrotonic acid butyl ester,
β-aminocrotonic acid β-methoxyethyl ester,
β-aminocrotonic acid β-ethoxyethyl ester,
β-aminocrotonic acid β-propoxyethyl ester,
β-aminocrotonic acid t-butyl ester,
β-aminocrotonic acid cyclohexyl ester and
β-amino-β-ethylacrylic acid ethyl ester.

Typical compounds of the present invention include:
2,6-Dimethyl-4-(2'-nitrophenyl)-1,4-dihydropyridine-3,5-dicarboxylic acid 3-methyl ester-5-isopropyl ester.
2,6-Dimethyl-4-(2'-cyanophenyl)-1,4-dihydropyridine-3,5-dicarboxylic acid 3-methyl ester-5-isopropyl ester.

2,6-Dimethyl-4-(2'-cyanophenyl)-1,4-dihydropyridine-3,5-dicarboxylic acid 3-ethyl ester-5-methyl ester.

2,6-Dimethyl-4-(2'-nitrophenyl)-1,4-dihydropyridine-3,5-dicarboxylic acid 3-ethyl ester-5-methyl ester.

2,6-Dimethyl-4-(2'-nitrophenyl)-1,4-dihydropyridine-3,5-dicarboxylic acid 3-methyl ester-5-$\beta$-methoxyethyl ester.

2,6-Dimethyl-4-(2'-nitrophenyl)-1,4-dihydropyridine-3,5-dicarboxylic acid 3-propyl ester -5-isopropyl ester.

2,6-Dimethyl-4-(2'-cyanophenyl)-1,4-dihydropyridine-3,5-dicarboxylic acid 3-allyl ester-5-isopropyl ester.

2,6-Dimethyl-4-(2'-nitrophenyl)-1,4-dihydropyridine-3,5-dicarboxylic acid 3-methyl ester-5-propargyl ester.

2,6-Dimethyl-4-(3'-cyanophenyl)-1,4-dihydropyridine-3,5-dicarboxylic acid 3-ethyl ester-5-methyl ester.

2,6-Dimethyl-4-(3'-cyanophenyl)-1,4-dihydropyridine-3,5-dicarboxylic acid 3-methyl ester-5-isopropyl ester.

2-Methyl-6-ethyl-4-(3'-nitrophenyl)-1,4-dihydropyridine-3,5-dicarboxylic acid 3-methyl ester-5-ethyl ester.

2-Methyl-6-isopropyl-4-(3'-nitrophenyl)-1,4-dihydropyridine-3,5-dicarboxylic acid 3-ethyl ester-5-isopropyl ester.

2,6-Dimethyl-4-(3'-nitrophenyl)-1,4-dihydropyridine-3,5-dicarboxylic acid 3-ethyl ester-5-$\beta$-methoxyethyl ester.

2,6-Dimethyl-4-(3'-nitrophenyl)-1,4-dihydropyridine-3,5-dicarboxylic acid 3-methyl ester-5-$\beta$-propoxyethyl ester.

2,6-Dimethyl-4-(3'-nitrophenyl)-1,4-dihydropyridine-3,5-dicarboxylic acid 3-methyl ester-5-isopropyl ester.

2,6-Dimethyl-4-(3'-nitrophenyl)-1,4-dihydropyridine-3,5-dicarboxylic acid 3-ethyl ester-5-propargyl ester.

2,6-Dimethyl-4-(3'-nitrophenyl)-1,4-dihydropyridine-3,5-dicarboxylic acid 3-ethyl ester-5-isopropyl ester.

2,6-Dimethyl-4-(3'-nitrophenyl)-1,4-dihydropyridine-3,5-dicarboxylic acid 3-methyl ester-5-allyl ester.

2,6-Dimethyl-4-(3'-nitro-6'-chlorophenyl)-1,4-dihydro-pyridine-3,5-dicarboxylic acid 3-methyl ester-5-isopropyl ester.

As previously stated, the compounds of this invention are valuable cardiovascular agents. In particular, the compounds upon administration cause a distinct and long-lasting dilation of the coronary vessels with a simultaneous nitrite-like reduction on the workload of the heart. At the same time, an anti-fibrillation effect and spasmolytic activity can be observed, the latter often manifesting itself not only in the smooth vascular muscle but also in the smooth muscle of the stomach, intestinal tract, urogenital tract and respiratory system. The compounds also exhibit hypotensive properties in the normo- and hypertonic animal.

The dose administered must of course be carefully adjusted to the age, weight and condition of the individual being treated, as well as the route of administration, dosage form andd regimen, and the result desired. A satisfactory result can, in certain instances, be obtained at a dose as low as 0.0005 mg/kg i.v. and 0.01 mg/kg p.o. The upper limit of the dosage range is about 10 mg/kg i.v. and 100 mg/kg p.o. Preferred ranges are from about 0.001 to about 1 mg/kg i.v. and from about 0.1 to about 10 mg/kg p.o.

In general it has proved advantageous to administer the dose divided among several administrations in order to achieve effective results. At times it is of course necessary to depart from these amounts, and in particular to do so as a function of the body weight of the test animal, the route of administration, the animal and its individual behavior towards the medicine, the type of its formulation, and/or the time or interval of administration. In some cases less than the minimum amount will suffice while in others, the upper limit must be exceeded.

The compounds of the present invention are administered parenterally or orally in any of the usual pharmaceutical forms. These include solid and liquid oral unit dosage forms such as tablets, capsules, powders, suspensions, solutions, syrups and the like, including sustained release preparations, and fluid injectable forms such as sterile solutions and suspensions. The term unit dosage form as used in this specification and the claims refer to physically discrete units to be administered in single or multiple dosage to animals, each unit containing a predetermined quantity of active material in association with the required diluent, carrier or vehicle. The quantity of active material is that calculated to produce the desired therapeutic effect upon administration of one or more of such units.

Powders are prepared by comminuting the compound to a suitable fine size and mixing with a similarly comminuted diluent pharmaceutical carrier such as an edible carbohydrate material as for example, starch. Sweetening, flavoring, preservative, dispersing and coloring agents can also be present.

Capsules are made by preparing a powder mixture as discribed above and filling formed gelatin sheaths. A lubricant such as talc, magnesium stearate and calcium stearate can be added to the powder mixture as an adjuvant before the filling operation; a glidant such as colloidal silica may be added to improve flow properties; a disintegrating or solubilizing agent may be added to improve the availability of the medicament when the capsule is ingested.

Tablets are made by preparing a powder mixture, granulating or slugging, adding a lubricant and disintegrant and pressing into tablets. A powder mixture is prepared by mixing the compound, suitably comminuted, with a diluent or base such as starch, sucrose, kaolin, dicalcium phosphate and the like. The powder mixture can be granulated by wetting with a binder such as syrup, starch paste, acacia mucilage or solutions of cellulosic or polymeric materials and forcing through a screen. As an alternative to granulating, the powder mixture can be run through the tablet machine and the resulting imperfectly formed slugs broken into granules. The granules can be lubricated to prevent sticking to the tablet forming dies by means of the addition of stearic acid, a stearate salt, talc or mineral oil. The lubricated mixture is then compressed into tablets. The medicaments can also be combined with free flowing inert carriers and compressed into tablets directly without going through the granulating or slugging steps. A protective coating consisting of a sealing coat of shellac, a coating of sugar or polymeric material and a polish coating of wax can be provided. Dyestuffs can be added to these coatings to distinguish different unit dosages.

Oral fluids such as syrups and elixirs can be prepared in unit dosage form so that a given quantity, e.g., a teaspoonful, contains a predetermined amount of the compound. Syrups can be prepared by dissolving the compound in a suitably flavored aqueous sucrose solution while elixirs are prepared through the use of a non-toxic alcoholic vehicle. Suspensions can be formulated by dispersing the compound in a non-toxic vehicle in which it is insoluble.

Fluid unit dosage forms for parenteral administration can be prepared by suspending or dissolving a measured amount of the compound in a non-toxic liquid vehicle suitable for injection such as an aqueous or oleaginous medium and sterilizing the suspension or solution. Alternatively a measured amount of the compound is placed in a vial and the vial and its contents are sterilized and sealed. An accompanying vial or vehicle can be provided for mixing prior to administration.

The pharmaceutical compositions of the invention can also contain other non-toxic adjuvants and modifiers such as dyes, buffering agents, preservatives, surfactants, emulsifiers, such as nonionic and anionic emulsifiers as, for example, polyoxyethylene-fatty acid esters, polyoxyethylene-fatty alcohol ethers, alkylsulphonates and arylsulphonates, or dispersing agents as, for example, lignin, sulfite waste lyes, methylcellulose, starch and polyvinyl pyrrolidone, perfumes, flavoring agents, preservatives and biocides.

Pharmaceutical compositions adapted for oral administration employ such ingredients as diluents and carriers, excipients and lubricants, as glucose, lactose, sucrose, corn and potato starch, sodium carboxymethyl cellulose, ethyl cellulose, cellulose acetate, powdered gum tragacanth, gelatin, alginic acid, agar, stearic acid, sodium, calcium and magnesium stearates, sodium lauryl sulfate, polyvinylpyrrolidone, sodium citrate, calcium carbonate, and dicalcium phosphate.

Pharmaceutical compositions adapted for parenteral injection employ such diluents and carriers as water and water-miscible organic solvents, in particular sesame oil, groundnut oil, aqueous propylene glycol, and N,N'-demethylformamide. Examples of pharmaceutical compositions of the invention adapted for parenteral administration include stirile isotonic saline aqueous solutions of the active ingredient, which can be buffered with a pharmaceutically acceptable buffer and are preferably pyrogen free.

The pharmacological properties of these compounds are conveniently observed in well-known animal models which parallel the desired clinical response. Similarly toxicity is low, as measured for example in the conventional $LD_{50}$ determination. This can be seen in the following table:

| Compound of Example: | Toxicity (Mouse) $DL_{50}$ mg/kg p.o. | Blood pressure effect (hypertensive rat) mg/kg p.o. |
| --- | --- | --- |
| 1 | 3000 | from 0.3 |
| 2 | 800 | from 1.0 |
| 3 | 2000 | from 1.0 |
| 4 | 630 | from 3.1 |
| 5 | 3000 | from 0.03 |
| 6 | 2000 | from 10.0 |
| 7 | 800 | from 3.1 |
| 8 | 3000 | from 1.0 |
| 9 | 1000 | from 3.1 |
| 10 | 3000 | from 1.0 |
| 11 | 800 | from 3.1 |
| 12 | 3000 | from 1.0 |
| 13 | 2000 | from 3.1 |
| 14 | 200 | from 0.3 |

-continued

| Compound of Example: | Toxicity (Mouse) $DL_{50}$ mg/kg p.o. | Blood pressure effect (hypertensive rat) mg/kg p.o. |
| --- | --- | --- |
| 15 | 200 | from 0.3 |
| 16 | 3000 | |
| 17 | 3000 | from 1.0 |
| 18 | 3000 | from 3.1 |
| 19 | 3000 | from 1.0 |
| 20 | 3000 | from 1.0 |
| 21 | 2000 | from 1.0 |
| 22 | 200 | from 1.0 |
| 24 | | from 0.3 |
| 25 | 800 | from 3.1 |
| 26 | 1000 | from 1.0 |
| 27 | 3000 | |
| 28 | 3000 | from 31.5 |
| 29 | 3000 | from 10.0 |
| 30 | 2000 | from 31.5 |
| 31 | 1000 | from 10.0 |
| 32 | 3000 | from 31.5 |
| 33 | 2000 | from 10.0 |
| 34 | 3000 | from 10.0 |
| 35 | 3000 | from 10.0 |
| 36 | 3000 | from 1.0 |
| 38 | 630 | from 31.5 |
| 39 | 2000 | from 1.0 |
| 41 | 3000 | |
| 42 | 320 | from 1.0 |
| 43 | 3000 | from 3.1 |
| 45 | 800 | from 100 |
| 46 | 3000 | from 10.0 |
| 47 | 3000 | from 100 |
| 50 | 1000 | from 0.3 |
| 51 | 2000 | from 1.0 |

The low dosages at which favorable hypotensive response is observed is also seen in the dosages at which a coronary effect is observed, as can be seen from the following tabulation:

| Compound of Example No. | Dose mg/kg i.v. | Compound of Example No. | Dose mg/kg i.v. |
| --- | --- | --- | --- |
| 1 | 0.001 | 28 | 0.05 |
| 2 | 0.001 | 29 | 0.1 |
| 3 | 0.005 | 30 | 0.1 |
| 4 | 0.001 | 31 | 0.05 |
| 5 | 0.001 | 32 | 0.1 |
| 6 | 0.005 | 33 | 0.2 |
| 7 | 0.01 | 34 | 0.05 |
| 8 | 0.005 | 35 | 0.01 |
| 9 | 0.01 | 36 | 0.2 |
| 10 | 0.005 | 38 | 0.2 |
| 11 | 0.005 | 39 | 0.2 |
| 12 | 0.01 | 40 | 0.05 |
| 13 | 0.001 | 41 | 3 |
| 14 | 0.0005 | 42 | 0.005 |
| 15 | 0.003 | 43 | 0.001 |
| 16 | 0.1 | 44 | 2 |
| 17 | 0.02 | 45 | 0.1 |
| 18 | 0.01 | 46 | 0.1 |
| 19 | 0.01 | 47 | 0.5 |
| 20 | 0.01 | 48 | 0.01 |
| 21 | 0.005 | 49 | 0.1 |
| 22 | 0.005 | 50 | 0.01 |
| 24 | 0.005 | 51 | 0.5 |
| 25 | 0.005 | 52 | 0.01 |
| 26 | 0.005 | 53 | 0.005 |
| 27 | 3 | | |

The following examples will serve to further typify the nature of this invention without being a limitation on the scope thereof, the scope being defined solely by the appended claims.

EXAMPLE 1

Boiling a solution of 13.4 g of 3'-nitrobenzylideneacetoacetic acid ethyl ester and 5.8 g of β-amino-crotonic acid methyl ester in 50 ml of ethanol for 10 hours yielded 2,6-dimethyl-4-(3'-nitrophenyl)-1,4-dihydropyridine-3,5-dicarboxylic acid 3-methyl ester-5-ethyl ester of melting point 158°C (from ethanol). Yield 67% of theory.

EXAMPLE 2

Heating a solution of 12.7 g of 3'-nitro-benzylideneacetoacetic acid methyl ester and 7.2 g of β-amino-crotonic acid propyl ester in 50 ml of methanol for 8 hours yielded 2,6-dimethyl-4-(3'-nitrophenyl)-1,4-dihydropyridine-3,5-dicarboxylic acid 3-methyl ester-5-isopropyl ester of melting point 147°C (from ethanol). Yield 70% of theory.

EXAMPLE 3

Boiling a solution of 14.0 g of 3'-nitrobenzylideneacetoacetic acid allyl ester and 5.8 g of β-aminocrotonic acid methyl ester in 50 ml of ethanol for 8 hours yielded 2,6-dimethyl-4-(3'-nitrophenyl)-1,4-dihyrdopyridine-3,5-dicarboxylic acid 3-methyl ester-5-allyl ester of melting point 110°C (from ethyl acetate/petroleum ether). Yield 63% of theory.

EXAMPLE 4

Boiling a solution of 12.7 g of 3'-nitrobenzylideneacetoacetic acid methyl ester, 7.0 g of acetoacetic acid propargyl ester and 6 ml of concentrated ammonia in 50 ml of ethanol for 8 hours yielded 2,6-dimethyl-4-(3'-nitrophenyl)-1,4-dihydropyridine-3,5-dicarboxylic acid 3-methyl ester-5-propargyl ester of melting point 111° – 113°C (from petroleum ether/ethyl acetate). Yield 70% of theory.

EXAMPLE 5

Heating a solution of 13.4 g of 3'-nitrobenzylideneacetoacetic acid ethyl ester and 7.2 g of β-amino-crotonic acid isopropyl ester in 50 ml of isopropanol for 10 hours yielded 2,6-dimethyl-4-(3'-nitrophenyl)-1,4-dihydropyridine- 3,5-dicarboxylic acid 3-ethyl ester-5-isopropyl ester of melting point 148°C (from ethanol). Yield 60% of theory.

EXAMPLE 6

Heating a solution of 13.4 g of 3-nitrobenzylideneacetoacetic acid ethyl ester, 9.2 g of acetoacetic acid β-propoxyethyl ester and 6 ml of concentrated ammonia in 50 ml of ethanol for 10 hours yielded 2,6-dimethyl-4-(3'-nitrophenyl)-1,4-dihydropyridine-3,5-dicarboxylic acid 3-ethyl ester-5-β-propoxyethyl ester of melting point 75°C (from petroleum ether/ethyl acetate). Yield 46% of theory.

EXAMPLE 7

Heating a solution of 14.9 g of 3'-nitrobenzylideneacetoacetic acid β-methoxyethyl ester and 6.5 g of β-aminocrotonic acid ethyl ester in 50 ml of methanol for 10 hours yielded 2,6-dimethyl-4-(3'-nitrophenyl)-1,4-dihydropyridine-3,5-dicarboxylic acid 3-ethyl ester-5-β-methoxyethyl ester of melting point 108°C (from ethanol/water). Yield 51% of theory.

EXAMPLE 8

Boiling a solution of 13.4 g of 3'-nitrobenzylideneacetoacetic acid ethyl ester, 7.1 g of acetoacetic acid allyl ester and 6 ml of concentrated ammonia in 50 ml of ethanol for 10 hours yielded 2,6-dimethyl-4-(3'-nitrophenyl)1,4-dihydropyridine-3,5-dicarboxylic acid 3-ethyl ester-5-allyl ester of melting point 125° – 126°C (from ethyl acetate/petroleum ether). Yield 55% of theory.

EXAMPLE 9

Boiling a solution of 13.4 g of 3'-nitrobenzylideneacetoacetic acid ethyl ester, 7.0 g of acetoacetic acid propargyl ester and 6.0 ml of concentrated ammonia in 50 ml of ethanol for 8 hours yielded 2,6-dimethyl-4-(3'-nitrophenyl)-1,4-dihydropyridine-3,5-dicarboxylic acid 3-ethyl ester-5-propargyl ester of melting point 132° – 133°C (from ethanol). Yield 54% of theory.

EXAMPLE 10

Boiling a solution of 13.4 g of 3'-nitrobenzylideneacetoacetic acid ethyl ester and 9.2 g of β-amino-crotonic acid cyclohexyl ester in 50 ml of methanol for 8 hours yielded 2,6-dimethyl-4-(3'-nitrophenyl)1,4-dihydropyridine-3,5-dicarboxylic acid 3-ethyl ester-5-cyclohexyl ester of melting point 135°C (from ethanol/water). Yield 44% of theory.

EXAMPLE 11

Heating a solution of 14.2 g of 3'-nitrobenzylideneacetoacetic acid isopropyl ester and 7.1 g of β-aminocrotonic acid allyl ester in 50 ml of ethanol for 10 hours yielded 2,6-dimethyl-4-(3'-nitrophenyl)-1,4-dihydropyridine-3,5-dicarboxylic acid 3-isopropyl ester-5-allyl ester of melting point 96° – 97°C (from ethanol/water). Yield 58% of theory.

EXAMPLE 12

Boiling a solution of 14.1 g of 3'-nitrobenzylideneacetoacetic acid isopropyl ester, 7.0 g of acetoacetic acid propargyl ester and 6 ml of concentrated ammonia in 50 ml of ethanol for 10 hours yielded 2,6-dimethyl-4-(3'-nitrophenyl)-1,4-dihydropyridine-3,5-dicarboxylic acid 3-isopropyl ester-5-propargyl ester of melting point 143.5°C (from ethyl acetate/petroleum ether). Yield 59% of theory.

EXAMPLE 13

Boiling a solution of 14.1 g of 3'-nitrobenzylideneacetoacetic acid isopropyl ester, 7.2 g of acetoacetic acid propyl ester and 6 ml of concentrated ammonia in 50 ml of ethanol for 8 hours yielded 2,6-dimethyl-4-(3'-nitrophenyl)-1,4-dihydropyridine-3,5-dicarboxylic acid 3-isopropyl esther-5-propyl ester of melting point 109° – 110°C (from ethanol/water). Yield 54% of theory.

EXAMPLE 14

Boiling a solution of 12.7 g of 2'-nitrobenzylideneacetoacetic acid methyl ester and 7.1 g of β-amino-crotonic acid isopropyl ester in 50 ml of methanol for 10 hours yielded 2,6-dimethyl-4-(2'-nitrophenyl)-1,4-dihydropyridine-3,5-dicarboxylic acid 3-methyl ester-5-isopropyl ester of melting point 174°C (from ethanol). Yield 48% of theory.

EXAMPLE 15

Heating a solution of 12.7 g of 2'-nitrobenzylideneacetoacetic acid methyl ester, 7.2 g of acetoacetic acid propyl ester and 6 ml of concentrated ammonia in 50 ml of ethanol for 8 hours yielded 2,6-dimethyl-4-(2'-nitrophenyl)-1,4-dihydropyridine-3,5-dicarboxylic acid 3-methyl ester-5-propyl ester of melting point 127° – 128°C (from isopropanol). Yield 54% of theory.

EXAMPLE 16

Boiling a solution of 13.4 g of 4'-nitrobenzylideneacetoacetic acid ethyl ester and 5.8 g of β-amino-crotonic acid methyl ester in 50 ml of ethanol for 8 hours yielded 2,6-dimethyl-4-(4'-nitrophenyl)-1,4-dihydropyridine-3,5-dicarboxylic acid 3-methyl ester-5-ethyl ester of melting point 150°C (from ethanol). Yield 85% of theory.

EXAMPLE 17

Boiling a solution of 15.2 g of 3'-nitro-6'-chlorobenzylideneacetoacetic acid ethyl ester and 5.8 g of β-amino-crotonic acid methyl ester in 50 ml of methanol for 10 hours yielded 2,6-dimethyl-4-(3'-nitro-6'-chlorophenyl)-1,4-dihydropyridine-3,5-dicarboxylic acid 3-methyl ester-5-ethyl ester of melting point 163° – 164°C (from ethanol/water). Yield 40% of theory.

EXAMPLE 18

Heating a solution of 15.2 g of 3'-nitro-6'-chlorobenzylideneacetoacetic acid ethyl ester and 7.2 g of β-amino-crotonic acid isopropyl ester in 50 ml of methanol for 8 hours yielded 2,6-dimethyl-4-(3'-nitro-6'-chlorophenyl)-1,4-dihydropyridine-3,5-dicarboxylic acid 3-ethyl ester-5-isopropyl ester of melting point 152°C (from petroleum ether/ethyl acetate). Yield 41% of theory.

EXAMPLE 19

Heating a solution of 14.5 g of 3'-nitro-6'-chlorobenzylideneacetoacetic acid methyl ester and 7.2 g of β-amino-crotonic acid isopropyl ester in 50 ml of methanol for 10 hours yielded 2,6-dimethyl-4-(3'-nitro-6'-chlorophenyl)1,4-dihydropyridine-3,5-dicarboxylic acid 3-methyl ester-5-isopropyl ester of melting point 163°C. Yield 54% of theory.

EXAMPLE 20

Boiling a solution of 13.4 g of 3'-nitrobenzylideneacetoacetic acid ethyl ester, 7.2 g of acetoacetic acid ethyl ester, 7.2 g of acetoacetic acid propyl ester and 6 ml of concentrated ammonia in 50 ml of ethanol for 8 hours yielded 2,6-dimethyl-4-(3'-nitrophenyl-1,4-dihydropyridine-3,5-dicarboxylic acid 3-ethyl ester-5-propyl ester of melting point 131° – 133°C (from petroleum ether/ethyl acetate). Yield 49% of theory.

EXAMPLE 21

Boiling a solution of 12.2 g of 2'-cyanobenzylideneacetoacetic acid ethyl ester and 5.8 g of β-amino-crotonic acid methyl ester in 50 ml of ethanol for 10 hours yielded 2,6-dimethyl-4-(2'-cyanophenyl)-1,4-dihydropyridine-3,5-dicarboxylic acid 3-methyl ester-5-ethyl ester of melting point 178°C (from ethanol). Yield 65% of theory.

EXAMPLE 22

Heating a solution of 12.2 g of 2'-cyanobenzylideneacetoacetic acid ethyl ester and 7.2 g of β-amino-crotonic acid isopropyl ester in 50 ml of ethanol for 8 hours yielded 2,6-dimethyl-4-(2'-cyanophenyl)-1,4-dihydropyridine-3,5-dicarboxylic acid 3-ethyl ester-5-isopropyl ester of melting point 152°C (from ethanol). Yield 49% of theory.

EXAMPLE 23

Boiling a solution of 12.2 g of 2'-cyanobenzylideneacetoacetic acid ethyl ester, 7.1 g of acetoacetic acid allyl ester and 6 ml of concentrated ammonia in 50 ml of ethanol for 10 hours yielded 2,6-dimethyl-4-(2'-cyanophenyl)-1,4-dihydropyridine-3,5-dicarboxylic acid 3-ethyl ester-5-allyl ester of melting point 148°C (from ethyl acetate/petroleum ether). Yield 24% of theory.

EXAMPLE 24

Boiling a solution of 12.9 of 2'-cyanobenzylideneacetoacetic acid propyl ester and 5.8 g of β-amino-crotonic acid methyl ester in 50 ml of methanol for 8 hours yielded 2,6-dimethyl-(2'-cyanophenyl)-1,4-dihydropyridine-3,5-dicarboxylic acid 3-methyl ester-5-propyl ester of melting point 188°C (from ethanol). Yield 51% of theory.

EXAMPLE 25

Heating a solution of 11.5 g of 3'-cyanobenzylideneacetoacetic acid methyl ester, 6.5 g of acetoacetic acid ethyl ester and 6 ml of concentrated ammonia in 50 ml of ethanol for 8 hours yielded 2,6-dimethyl-4-(3'-cyanophenyl)-1,4-dihydropyridine-3,5-dicarboxylic acid 3-methyl ester-5-ethyl ester of melting point 150°C (from ethanol). Yield 68% of theory.

EXAMPLE 26

Boiling a solution of 12.2 g of 3'-cyanobenzylideneacetoacetic acid ethyl ester and 7.1 g of β-amino-crotonic acid isopropyl ester in 50 ml of ethanol for 8 hours yielded 2,6-dimethyl-4-(3'-cyanophenyl)-1,4-dihydropyridine-3,5-dicarboxylic acid 3-ethyl ester-5-isopropyl ester of melting point 133° – 134°C (from petroleum ether/ethyl acetate). Yield 55% of theory.

EXAMPLE 27

Heating a solution of 12.5 g of 4'-methylmercaptobenzylideneacetoacetic acid methyl ester, 6.5 g of acetoacetic acid ethyl ester and 6 ml of concentrated ammonia in 50 ml of ethanol for 10 hours yielded 2,6-dimethyl-4-(4'-methylmercaptophenyl)-1,4-dihydropyridine-3,5-dicarboxylic acid 3-methyl ester-5-ethyl ester of melting point 163°C (from ethanol). Yield 60% of theory.

EXAMPLE 28

Boiling a solution of 10.5 g of 2'-thenylmethylideneacetoacetic acid methyl ester and 6.5 g of β-amino-crotonic acid ethyl ester in 50 ml of ethanol for 10 hours yielded 2,6-dimethyl-4-(2'-thenyl)-1,4-dihydropyridine-3,5-dicarboxylic acid 3-methyl ester-5-ethyl ester of melting point 142°C (from methanol). Yield 45% of theory.

EXAMPLE 29

Heating a solution of 10.5 g of 2'-thenylmethylideneacetoacetic acid methyl ester and 7.2 g of β-aminocrotonic acid isopropyl ester in 50 ml of methanol for 8 hours yielded 2,5-dimethyl-4-(2'-thenyl)-1,4-dihydropyridine-3,5-dicarboxylic acid 3-methyl ester-5-isopropyl ester of melting point 121° – 122°C (from ethanol). Yield 41% of theory.

EXAMPLE 30

Boiling a solution of 10.9 g of α-pyridylmethylideneacetoacetic acid ethyl ester and 5.8 g of β-aminocrotonic acid methyl ester in 50 ml of ethanol for 10 hours yielded 2,6-dimethyl-4-(α-pyridyl)-1,4-dihydropyridine-3,5-dicarboxylic acid 3-methyl ester-5-ethyl ester of melting point 199° – 200°C (from ethanol). Yield 63% of theory.

EXAMPLE 31

Heating a solution of 10.2 g of α-pyridylmethylideneacetoacetic acid methyl ester and 7.2 g of β-aminocrotonic acid isoprophyl ester in 50 ml of ethanol for 10 hours yielded 2,6-dimethyl-4-(α-pyridyl)-1,4-dihydropyridine-3,5-dicarboxylic acid 3-methyl ester-5-isopropyl ester of melting point 188°C (from ethanol). Yield 40% of theory.

EXAMPLE 32

Boiling a solution of 11.6 g of α-pyridylmethylideneacetoacetic acid isopropyl ester, 7.2 g of acetoacetic acid propyl ester and 6 ml of concentrated ammonia in 50 ml of ethanol for 8 hours yielded 2,6-dimethyl-4-(β-pyridyl)-1,4-dihydropyridine-3,5-dicarboxylic acid 3-propyl ester-5-isopropyl ester of melting point 153° – 154°C (from ethyl acetate/petroleum ether). Yield 45% of theory.

EXAMPLE 33

Heating a solution of 10.2 g of α-pyridylmethylideneacetoacetic acid methyl ester and 7.0 g of β-aminocrotonic acid propargyl ester in 50 ml of ethanol for 10 hours yielded 2,6-dimethyl-4-(α-pyridyl)-1,4-dihydropyridine-3,5-dicarboxylic acid 3-methyl ester-5-propargyl ester of melting point 194° – 195°C (from ethanol). Yield 42% of theory.

EXAMPLE 34

Heating a solution of 13.4 g of α-naphthylideneacetoacetic acid ethyl ester and 7.2 g of β-amino-crotonic acid isopropyl ester in 50 ml of ethanol for 10 hours yielded 2,6-dimethyl-4-(α-naphthyl)-1,4-dihydropyridine-3,5-dicarboxylic acid 3-ethyl ester-5-isopropyl ester of melting point 167°C. Yield 38% of theory.

EXAMPLE 35

Boiling a solution of 13.4 g of α-naphthylideneacetoacetic acid ethyl ester and 5.8 g of β-amino-crotonic acid methyl ester in 50 ml of methanol for 8 hours yielded 2,6-dimethyl-4-(α-naphthyl)-1,4-dihydropyridine-3,5-dicarboxylic acid 3-ethyl ester-5-methyl ester of melting point 196°– 197°C (from ethanol). Yield 45% of theory.

EXAMPLE 36

Heating a solution of 12.7 g of 4'-quinolylmethylideneacetoacetic acid methyl ester and 6.5 g of β-aminocrotonic acid ethyl ester in 50 ml of methanol for 8 hours yielded 2,6-dimethyl-4-(4'-quinolyl)-1,4-dihydropyridine-3,5-dicarboxylic acid 3-methyl ester-5-ethyl ester of melting point 208°C (from ethanol). Yield 74% of theory.

EXAMPLE 37

Boiling a solution of 9.7 g of 2'-pyrrylmethylideneacetoacetic acid methyl ester, 6.5 g of acetoacetic acid ethyl ester and 6 ml of concentrated ammonia in 50 ml of ethanol for 10 hours yielded 2,6-dimethyl-4-(2'-pyrryl)-1,4-dihydropyridine-3,5-dicarboxylic acid 3-methyl ester-5-ethyl ester of melting point 239°C (from diethyl ether). Yield 36% of theory.

EXAMPLE 38

Heating a solution of 10.2 g of β-pyridylmethylideneacetoacetic acid methyl ester and 6.5 g of β-aminocrotonic acid ethyl ester in 50 ml of ethanol for 8 hours yielded 2,6-dimethyl-4-(β-pyridyl)-1,4-dihydropyridine-3,5-dicarboxylic acid 3-methyl ester-5-ethyl ester of melting point 191° – 192°C (from ethanol). Yield 59% of theory.

EXAMPLE 39

Boiling a solution of 11.6 g of β-pyridylmethylideneacetoacetic acid isopropyl ester and 5.8 g of β-aminocrotonic acid methyl ester in 50 ml of ethanol for 10 hours yielded 2,5-dimethyl-4-(β-pyridyl)-1,4-dihydropyridine-3,5-dicarboxylic acid 3-methyl ester-5-isopropyl ester of melting point 164° – 165°C (from methanol). Yield 52% of theory.

EXAMPLE 40

By a solution of 12.8 g of quinolyl-8-methylidene acetoacetic acid methyl ester and 7.2 g amino-crotonic acid isopropyl ester in 80 ml ethanol under reflux for 5 hours, 2,6-dimethyl-4-(8'-quinolyl)-1,4-dihydropyridine-3,5-dicarboxylic acid 3-methyl ester 5-isopropyl ester of melting point 178° – 179°C was obtained (alcohol). Yield 69% of theory.

EXAMPLE 41

After 8 hours' heating of a solution of 12.8 grams isoquinolyl-3-methylamine acetoacetic acid methyl ester and 6.5 g amino-crotonic acid ethyl ester in 100 ml ethanol, 2,6-dimethyl-4-(3'-isoquinolyl)-3,5-dicarboxylic acid 3-methyl ester 5-ethyl ester of melting point 206°C (ethanol) were obtained. Yield 73% of theory.

EXAMPLE 42

By 10 hours' heating of a solution of 12.2 g 3'-cyanobenzylamine acetoacetic acid ethyl ester and 7.0 g amino-crotonic acid propargyl ester in 80 ml isopropanol, 2,6-dimethyl-4-(3'-cyanophenyl)-1,4-dihydropyridine-3,5-dicarboxylic acid-3-methyl ester 5-propargyl ester of melting point 144° – 145°C (acetic ester/petroleum ether) were obtained. Yield 63% of theory.

EXAMPLE 43

After 8 hours' boiling of a solution of 3.8 grams of 3'-nitro-benzylideneacetoacetic acid isopropyl ester, 8 grams of acetoacetic acid β-methoxyethyl ester and 6 ml conc. ammonia in 80 ml ethanol under reflux, 2,6-dimethyl-4-(3'-nitro-phenyl)-1,4-dihydropyridine 3-β-methoxyethyl ester 5-isopropyl ester of melting point 125°C (petroleum ether/acetic esther) was obtained. Yield 49% of theory.

EXAMPLE 44

After 7 hours' boiling of a solution of 3.5 g β-naphthylidene acetoacetic acid ethyl ester and 5.8 g aminocrotonic acid methyl ester in 80 ml ethanol, 2,6-dimethyl-4-(β-naphthyl)-1,4-dihydropyridine-3,5-dicarboxylic acid 3-methyl ester 5-ethyl ester of melting point 140° – 142°C (ethanol) was obtained. Yield 47% of theory.

EXAMPLE 45

By 8 hours' heating of a solution of 9.7 g 2'-furfurylidene acetoacetic acid methyl ester, 7.1 acetoacetic acid allyl ester and 6 ml conc. ammonia in 100 ml ethanol, 2,6-dimethyl-4-(2'-furyl)-1,4-dihydropyridine 3,5-dicarboxylic acid 3-methyl ester 5-allyl ester of melting point 134° – 135°C (ethanol) was obtained. Yield 59% of theory.

EXAMPLE 46

By 10 hours' heating of a solution of 14.0 g 4,6-dimethoxypyrimidine 5-methylideneacetoacetic acid ethyl ester and 5.8 g amino-crotonic acid methyl ester in 100 ml ethanol, 2,6-dimethyl-4-(4',6'-dimethoxypyrimidyl-5')-1,4-dihydropyridine-3,5-dicarboxylic acid 3-methyl ester 5-ethyl ester of melting point 245°C (ethanol/water) was obtained. Yield 68% of theory.

EXAMPLE 47

By 8 hours' boiling of a solution of 9.7 g 2'-furfurylidene acetoacetic acid methyl ester and 6.5 g aminocrotonic acid ethyl ester in 80 ml ethanol, 2,6-dimethyl-4-(2'-furyl)-1,4-dihydropyridine-3,5-dicarboxylic acid 3-methyl ester 5-ethyl ester of melting point 154° – 155°C (acetic ester) was obtained. Yield 66% of theory.

EXAMPLE 48

After 10 hours' heating of a solution of 12.2 g 2'-cyanobenzylidene acetoacetic acid ethyl ester, 7.2 g acetoacetic n-propyl ester and 6 ml conc. ammonia in 80 ml ethanol under reflux, 2,6-dimethyl-4-(2'-cyanophenyl)-1,4-dihydropyridine-3,5-dicarboxylic acid 3-ethyl ester 5-n-propyl ester of melting point 156°C (diethyl ether) was obtained. Yield 47% of theory.

EXAMPLE 49

After 6 hours' heating of a solution of 12.8 g isoquinolyl-1-methylidene acetoacetic acid methyl ester and 7.2 g amino-crotonic acid isopropyl ester in 80 ml ethanol, 2,6-dimethyl-4-(1'-isoquinolyl)-1,4-dihydropyridine-3,5-dicarboxylic acid 3-methyl ester 5-isopropyl ester of melting point 204°C (ethanol) was obtained. Yield 78% of theory.

EXAMPLE 50

After 8 hours' boiling of a solution of 12.5 g 3'-nitrobenzylidene-acetoacetic acid methyl ester and 7.2 g β-ethyl-β-aminoacrylic acid ethyl ester in 70 ml ethanol, 2-methyl-6-ethyl-4-(3'-nitrophenyl) 1,4-dihydropyridine-3,5-dicarboxylic acid 3-methyl ester 5-ethyl ester of melting point 123°C (acetic ester/petroleum) was obtained. Yield 71% of theory.

EXAMPLE 51

By 8 hours' heating of a solution of 11.7 g 6'-methylpyridyl-2-methylidene-acetoacetic acid ethyl ester and 5.8 g amino-crotonic acid methyl ester in 80 ml ethanol, 2,6-dimethyl-4-(6'-methylpyridyl-2')-1,4-dihydropyridine 3,5-dicarboxylic acid-3-methyl ester 5-ethyl ester of melting point 162°C (ethanol) was obtained. Yield 62% of theory.

EXAMPLE 52

By 9 hours' heating of a solution of 12.5 g 3'-nitrobenzylidene acetoacetic acid methyl ester, 8.0 g acetoacetic acid β-methoxyethyl ester and 6 ml conc. ammonia in 80 ml ethanol, 2,6-dimethyl-4-(3'-nitrophenyl)-1,4-dihydropyridine 3,5-dicarboxylic acid 3-β-methoxyethyl ester 5-methyl ester of melting point 204°C (acetic ester/petroleum ether) was obtained. Yield 50% of theory.

EXAMPLE 53

After 8 hours' heating of a solution of 13.2 g 2'-nitrobenzylidene acetoacetic acid ethyl ester and 5.8 g amino-crotonic acid methyl ester in 60 ml ethanol, 2,6-dimethyl-4-(2'-nitrophenyl)-1,4-dihydropyridine-3,5-dicarboxylic acid 3-methyl ester 5-ethyl ester of melting point 117°C (acetic ester/petroleum ether) was obtained. Yield 58% of theory.

What is claimed is:

1. A pharmaceutical composition useful for effecting coronary vascular dilation and for treating hypertension which comprises a coronary vascular dilating effective amount or an antihypertensive amount of a compound of the formula:

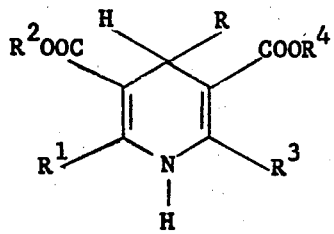

wherein
R is mono or disubstituted phenyl in which the substituents are selected from the group consisting of nitro, cyano, azido, —S(O)$_n$-lower alkyl in which $n$ has a value of 0, 1 or 2, lower alkyl, lower alkoxy and halogeno, at least one of said substituents being nitro, cyano, azido or —S(O)$_n$-lower alkyl; or a member selected from the group consisting of naphthyl, pyridyl, methylpyridyl, thenyl, furyl, and pyrryl;
each of $R^1$ and $R^3$, independent of the other, is hydrogen or lower alkyl;
$R^2$ is lower alkyl, lower alkenyl, lower alkynyl, or lower alkoxy(lower alkyl);
$R^4$ is lower alkyl, lower alkenyl, lower alkynyl, or lower alkoxy(lower alkyl), $R^4$ being different from $R^2$,
or a pharmaceutically acceptable acid addition salt thereof, in combination with a pharmaceutically acceptable non-toxic inert carrier.

2. A pharmaceutical composition according to claim 1 wherein each of $R^1$ and $R^3$ is lower alkyl and $R^2$ is lower alkyl.

3. A pharmaceutical composition according to claim 1 wherein $R^1$ and $R^3$ are each methyl, $R^2$ is methyl, ethyl, propyl or isopropyl and $R^4$ is different from $R^2$ and is methyl, ethyl, propyl, isopropyl, allyl, propargyl, propoxyethyl, methoxyethyl or cyclohexyl.

4. A pharmaceutical composition according to claim 3 wherein R is phenyl substituted by cyano, nitro or methylmercapto and further unsubstituted or substituted by chloro.

5. A pharmaceutical composition according to claim 3 wherein R is pyridyl, pyrryl, furyl, or pyrimidyl.

6. A pharmaceutical composition according to claim 3 wherein R is naphthyl, quinolyl or isoquinolyl.

7. A pharmaceutical composition according to claim 1 in oral administration form.

8. A pharmaceutical composition according to claim 1 wherein the compound is 2,6-dimethyl-4-(2'-nitrophenyl)-1,4-dihydropyridine-3,5-dicarboxylic acid 3-methyl ester-5-isopropyl ester.

9. A pharmaceutical composition according to claim 1 wherein the compound is 2,6-dimethyl-4-(3'-nitrophenyl)-1,4-dihydropyridine-3,5-dicarboxylic acid 3-methyl ester-5-ethyl ester.

10. A pharmaceutical composition according to claim 1 wherein the compound is 2,6-dimethyl-4-(3'-nitrophenyl)-1,4-dihydropyridine-3,5-dicarboxylic acid 3-methyl ester-5-isopropyl ester.

11. A pharmaceutical composition according to claim 1 wherein the compound is 2,6-dimethyl-4-(3'-nitrophenyl)-1,4-dihydropyridine 3-$\beta$-methoxyethyl ester-5-isopropyl ester.

12. A pharmaceutical composition according to claim 1 wherein the compound is 2,6-dimethyl-4-(4'-nitrophenyl)-1,4-dihydropyridine-3,5-dicarboxylic acid 3-methyl ester-5-ethyl ester.

13. A pharmaceutical composition according to claim 1 wherein the compound is 2,6-dimethyl-4-($\alpha$-pyridyl)-1,4-dihydropyridine-3,5-dicarboxylic acid 3-methyl ester-5-isopropyl ester.

14. A pharmaceutical composition according to claim 1 wherein the compound is 2,6-dimethyl-4-($\alpha$-pyridyl)-1,4-dihydropyridine-3,5-dicarboxylic acid 3-methyl ester-5-propargyl ester.

15. A method of effecting coronary vascular dilation in humans and animals which comprises administering to such human or animal an amount of a compound of the formula:

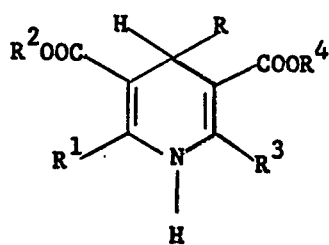

wherein

R is mono or disubstituted phenyl in which the substituents are selected from the group consisting of nitro, cyano, azido, —S(O)$_n$-lower alkyl in which $n$ has a value of 0, 1 or 2, lower alkyl, lower alkoxy and halogeno, at least one of said substituents being nitro, cyano, azido or —S(O)$_n$-lower alkyl; or a member selected from the group consisting of naphthyl, pyridyl, methylpyridyl, thenyl, furyl, and pyrryl;

each of R$^1$ and R$^3$, independent of the other, is hydrogen or lower alkyl;

R$^2$ is lower alkyl, lower alkenyl, lower alkynyl, or lower alkoxy(lower alkyl);

R$^4$ is lower alkyl, lower alkenyl, lower alkynyl, or lower alkoxy(lower alkyl), R$^4$ being different from R$^2$, or a pharmaceutically acceptable acid addition salt thereof, sufficient to effect coronary vascular dilation.

16. A method according to claim 15 wherein each of R$^1$ and R$^3$ is lower alkyl and R$^2$ is lower alkyl.

17. A method according to claim 15 wherein R$^1$ and R$^3$ are each methyl, R$^2$ is methyl, ethyl, propyl or isopropyl and R$^4$ is different from R$^2$ and is methyl, ethyl, propyl, isopropyl, allyl, propargyl, propoxyethyl, methoxyethyl or cyclohexyl.

18. A method according to claim 15 wherein R is phenyl substituted by cyano, nitro or methylmercapto and further unsubstituted or substituted by chloro.

19. A method according to claim 15 wherein R is pyridyl, pyrryl or furyl.

20. A method according to claim 15 wherein R is naphthyl.

21. A method according to claim 15 wherein the administration is oral.

22. The method according to claim 15 wherein the compound is 2,6-dimethyl-4-(2'-nitrophenyl)-1,4-dihydropyridine-3,5-dicarboxylic acid 3-methyl ester-5-isopropyl ester.

23. The method according to claim 15 wherein the compound is 2,6-dimethyl-4-(3'-nitrophenyl)-1,4-dihydropyridine-3,5-dicarboxylic acid 3-methyl ester-5-ethyl ester.

24. The method according to claim 15 wherein the compound is 2,6-dimethyl-4-(3'-nitrophenyl)-1,4-dihydropyridine-3,5-dicarboxylic acid 3-methyl ester-5-isopropyl ester.

25. The method according to claim 15 wherein the compound is 2,6-dimethyl-4-(3'-nitrophenyl)-1,4-dihydropyridine 3-$\beta$-methoxyethyl ester-5-isopropyl ester.

26. The method according to claim 15 wherein the compound is 2,6-dimethyl-4-(4'-nitrophenyl)-1,4-dihydropyridine-3,5-dicarboxylic acid 3-methyl ester-5-ethyl ester.

27. The method according to claim 15 wherein the compound is 2,6-dimethyl-4-($\alpha$-pyridyl)-1,4-dihydropyridine-3,5-dicarboxylic acid 3-methyl ester-5-isopropyl ester.

28. The method according to claim 15 wherein the compound is 2,6-dimethyl-4-($\alpha$-pyridyl)-1,4-dihydropyridine-3,5-dicarboxylic acid 3-methyl ester-5-propargyl ester.

* * * * *